United States Patent [19]

Degnan

[11] Patent Number: 4,669,980
[45] Date of Patent: Jun. 2, 1987

[54] ORTHODONTIC APPLIANCE

[76] Inventor: Edward V. Degnan, 510 CyCare Plz. Dubuque, Iowa 52001

[21] Appl. No.: 668,191

[22] Filed: Nov. 5, 1984

[51] Int. Cl.$^4$ .............................................. A61C 3/00
[52] U.S. Cl. ............................................ 433/8; 433/9; 433/16; 433/17
[58] Field of Search ..................... 433/8, 9, 10, 11, 14, 433/15, 16, 17, 18, 20, 21, 22

[56] References Cited

U.S. PATENT DOCUMENTS

| | | | |
|---|---|---|---|
| 1,821,171 | 9/1931 | Atkinson | 433/14 |
| 2,230,315 | 2/1941 | Winslow | 433/11 |
| 2,495,692 | 1/1950 | Brusse | 433/20 |
| 3,134,171 | 5/1964 | Kessler | 433/14 |
| 3,660,900 | 5/1972 | Andrews | 433/16 |
| 3,762,050 | 10/1973 | Dal Pont | 433/20 |
| 3,775,850 | 12/1973 | Northcutt | 433/9 |
| 3,874,080 | 4/1975 | Wallshein | 433/17 |
| 3,975,824 | 8/1976 | Lee | 433/14 |
| 4,243,386 | 1/1981 | Kawaguchi | 433/9 |
| 4,248,588 | 2/1981 | Hanson | 433/11 |
| 4,322,206 | 3/1982 | Reynolds | 433/8 |
| 4,354,834 | 10/1982 | Wilson | 433/11 |
| 4,386,908 | 6/1983 | Kurz | 433/9 |
| 4,575,337 | 3/1986 | Fujita | 433/8 |

FOREIGN PATENT DOCUMENTS

| | | | |
|---|---|---|---|
| 45687 | 5/1932 | Denmark | 433/17 |
| 1129016 | 1/1957 | France | 433/17 |

Primary Examiner—John J. Wilson
Attorney, Agent, or Firm—Beveridge, DeGrandi & Weilacher

[57] ABSTRACT

An orthodontic appliance comprising: an orthodontic channel bracket having two channels therein at right angles to each other in adjacent sides of the bracket; an orthodontic tube bracket providing the static components of a spring latch or locking mechanism; a supplemental tube bracket providing the movable components of a spring latch or locking mechanism, and removable and replacable molar tube components of an orthodontic appliance; and an orthodontic arch wire movable spring latch component mechanism.

18 Claims, 24 Drawing Figures

FIG. 15
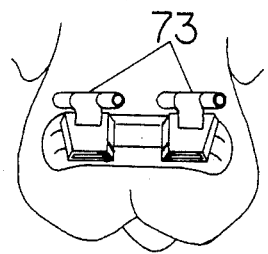
FIG. 16
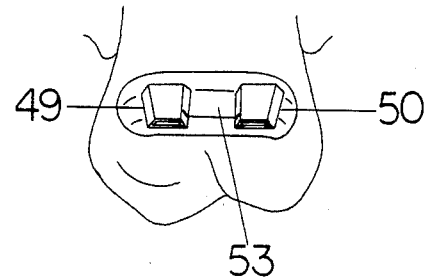
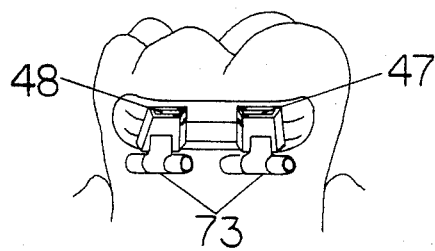
FIG. 17
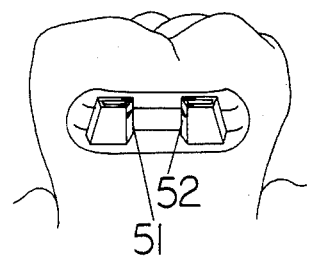
FIG. 18
FIG. 19    FIG. 20    FIG. 21
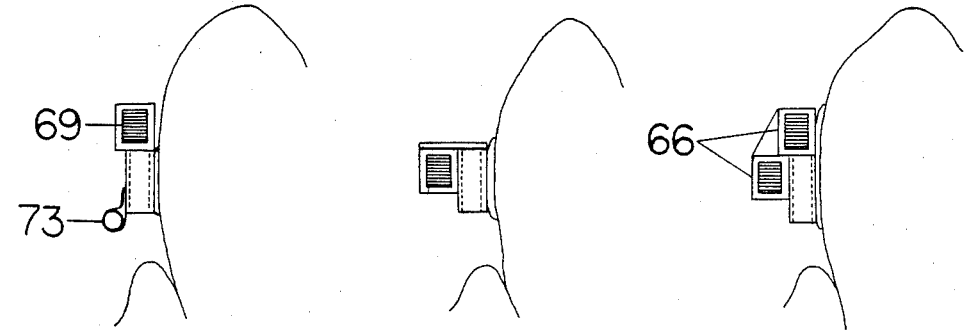

FIG. 22
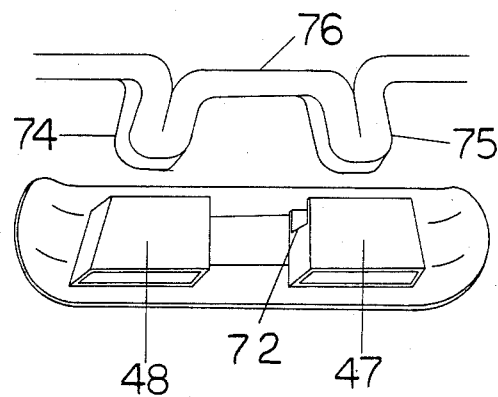
FIG. 23
FIG. 24
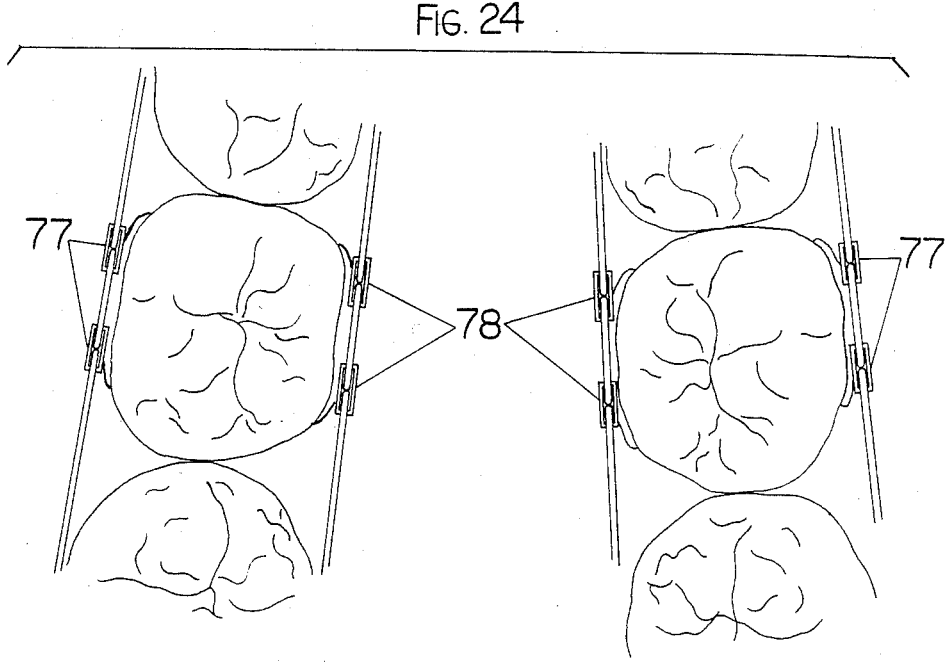

ORTHODONTIC APPLIANCE

FIELD OF THE INVENTION

This invention pertains in general to an orthodontic appliance and more particularly to the primary components of the orthodontic appliance. The primary components are: an orthodontic channel bracket, an orthodontic tube bracket, a supplemental tube bracket, and an orthodontic arch wire.

BACKGROUND AND PRIOR ART

The prior art reveals various types of orthodontic brackets for use as components of an orthodontic appliance. The orthodontic brackets of the prior art have channels in their surfaces, and various other means of receiving and retaining an orthodontic arch wire in relation to the orthodontic bracket. Various vectors of force are used in providing orthodontic treatment. Some of these vectors of force exerted on the teeth are: torquing, tipping, rotational, intrusive, extrusive, and facial and lingual directional forces. The orthodontic brackets of the prior art each have characteristics that are useful in providing some of these forces. None of the brackets of the prior art provide the design and configuration that can be utilized to provide precisely and efficiently all of the vectors of force mentioned above.

There are various ways used to overcome inefficiencies of particular brackets of the prior art. To overcome a lack of efficiency to produce a rotational force, the prior art reveals the use of wedges ligated in relation to the bracket, tooth, and arch wire; and orthodontic brackets with increased mesial-distal width, ligated to an orthodontic arch wire. These methods lack the efficiency and preciseness obtained in producing a rotational force by confining an orthodontic arch wire within the rectangular walls of a channel traversing an orthodontic bracket, and utilizing the elasticity of the arch wire to exert precise and efficient rotational forces along the occlusal-apical axis of a tooth. The orthodontic channel bracket of this invention provides a precise and efficient means to produce rotational forces along the occlusal-apical axis of a tooth.

The orthodontic brackets of the prior art are designed to follow very closely and continuously the surface of the tooth upon which they are placed. There are variations in the size and contour of the clinical crown of teeth in one person as compared to another person. These variations adversely affect the stability and fit of brackets that follow closely and continuously the surface of the crowns of teeth.

Adhesive materials are used to attach the orthodontic brackets to teeth. A bracket that follows the tooth surface very closely and continuously will cause the adhesive materials to be squashed upon the surface of the tooth and obscure the precise contact of the bracket with the tooth, and cause the adhesive material to flow out from between the interfacing areas of the bracket and the tooth surface.

The orthodontic brackets of this invention specifically address these problems.

The orthodontic tube brackets of the prior art are rigid in design and do not provide a means of changing the tube or tubes of the bracket, without the complete removal of the tube bracket from the surface of the tooth. This invention provides a means of changing some of the tube components used as part of an orthodontic appliance, without the removal of the tube bracket from the tooth to which it has been attached.

Various types of orthodontic arch wires are revealed in the prior art. This invention provides an orthodontic arch wire with a design and configuration to be used with the orthodontic tube bracket and the orthodontic channel brackets of the invention.

The orthodontic appliance of this invention provides improved and new components of an orthodontic appliance.

BRIEF SUMMARY OF THE INVENTION

The invention is an orthodontic appliance. The four principle components of the invention are: an orthodontic channel bracket, an orthodontic tube bracket, a supplemental tube bracket, and an orthodontic arch wire.

The orthodontic channel bracket of the invention provides a vertical channel and a horizontal channel in the channel bracket. The vertical channel traverses the occlusal aspect of the bracket from mesial to distal, with the open side of the channel facing occlusally. The horizontal channel traverses the bracket surface from mesial to distal with the open side of the channel facing facially, when the bracket is placed upon the facial side of a tooth, and lingually when the bracket is placed upon the lingual side of a tooth. The presence of a vertical channel and a horizontal channel in the channel bracket provides for the confining of an orthodontic arch wire in each or both channels of the bracket in a manner to produce a full spectrum of orthodontic forces upon a tooth.

In addition to the vertical and horizontal channels, the bracket also has areas to accept orthodontic ligatures at the gingival and occlusal areas of the bracket. The area to accept ligatures is larger at the gingival area of the bracket, to accommodate more than a single ligature, when necessary, in treatment procedures using the channel bracket of this invention.

The entire side of the channel bracket that interfaces with the surface of a tooth is not intended to be in full and continuous contact with the surface of the tooth. The interfacing surface of the bracket is designed to have selected areas of this surface to rest firmly upon the surface of the tooth. The remaining areas of the interfacing surface are progressively concave in shape, from the margins of the bracket toward the center area of the bracket. The design and configuration of this interfacing side of the bracket provides improved fit and stability of the bracket, by decreasing the effects caused by variations in the shape and size of the surfaces of teeth, of one person as compared to another person.

The presence of the vertical channel, in addition to the horizontal channel, traversing the channel bracket from mesial to distal, and the design and configuration of the side of the channel bracket that interfaces with the surface of the tooth, provides a new shape and usefulness of the channel bracket.

The invention provides a tube bracket and a supplemental tube bracket. The tube bracket is attached to the surface of a tooth. The supplemental tube bracket has components that fit into the tube bracket. The supplemental tube bracket and its components can be removed from the tube bracket, without removing the tube bracket from the surface of the tooth to which it is attached.

The supplemental tube bracket may have as its components a single divided tube or two divided tubes, horizontal to the occlusal plane. Each divided tube can receive an orthodontic arch wire.

The orthodontic arch wire of the invention has a design and configuration to be used with the tube bracket of the invention. The arch wire has a first-mesial and a second-distal post-shaped area and an interval of space between these two post-shaped areas. The angular relation of these two post-shaped areas to each other is identical to the angular relation of the two post-shaped areas of the supplemental tube bracket that are receivable into the first-mesial and second-distal occlusal-gingival tubes of the tube bracket that is attached to a tooth. The portion of the arch wire that extends from the section of the arch wire designed to intercouple with the tube bracket can be round, square, or rectangular in diameter, as it extends along the teeth of the dental arch.

The advantages, usefulness, and newness of the orthodontic appliance of the invention and its components will become apparent from the descriptive text and the accompanying drawings.

DESCRIPTION OF THE DRAWINGS

FIG. 15 is an illustration of an orthodontic tube bracket upon the facial surface of a maxillary molar tooth and a divided horizontal tube attached to the facial-gingival area of the occlusal-gingival tubes of the orthodontic tube bracket.

FIG. 16 is an illustration of an orthodontic tube bracket upon the lingual surface of a maxillary molar tooth.

FIG. 17 is an illustration of an orthodontic tube bracket upon the facial surface of a mandibular molar tooth and a divided horizontal tube attached to the facial-gingival area of the occlusal-gingival tubes of the orthodontic tube bracket.

FIG. 18 is an illustration of an orthodontic tube bracket upon the lingual surface of a mandibular molar tooth.

FIG. 19 is an illustration of a mesial view of an orthodontic tube bracket attached to the surface of a molar tooth, with the base of the supplemental tube bracket having been intercoupled therein, and the horizontal tube of the supplemental tube bracket upon the orthodontic tube bracket.

FIG. 20 is an illustration of a mesial view of an orthodontic tube bracket attached to the surface of a molar tooth, with the base of the supplemental tube bracket having been intercoupled into the orthodontic tube bracket, and the horizontal tube of the supplemental tube bracket positioned upon the lateral surface of the orthodontic tube bracket.

FIG. 21 is an illustration of a mesial view of an orthodontic tube bracket attached to the surface of a molar tooth, with the base of the supplemental tube bracket having been intercoupled into the orthodontic tube bracket and the two horizontal tubes of the supplemental tube bracket positioned respectively upon the occlusal aspect of the orthodontic tube bracket and upon the lateral aspect of the orthodontic tube bracket.

FIG. 22 is an illustration of the intercoupling portion of an orthodontic arch wire of the invention and a portion of the mesial and distal portions of the orthodontic arch wire extending from the intercoupling area of the orthodontic arch wire.

FIG. 23 is an illustration of the orthodontic tube bracket of the invention, into which the orthodontic arch wire of the invention is intercoupled.

FIG. 24 is an illustration of an occlusal view of orthodontic tube brackets attached upon the facial and lingual surfaces of molar teeth, and with the intercoupling segment of an orthodontic arch wire intercoupled into each orthodontic tube bracket, respectively, and showing a portion of the mesial and distal extensions of each arch wire from the area of intercoupling of each arch wire with the respective orthodontic tube bracket.

EMBODIMENT OF THE INVENTION

The four primary components of the orthodontic appliance of the invention will be described, and the design, configuration, and function of the components will be presented.

The four components are: an orthodontic channel bracket, an orthodontic tube bracket, a supplemental tube bracket, and an orthodontic arch wire.

Figure 1:
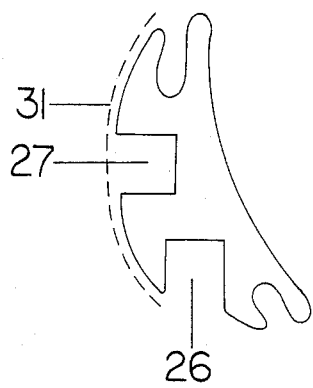
FIG. 1 is an illustration of a lateral view of an orthodontic channel bracket for placement upon the lingual surface of a maxillary incisor tooth.
Figure 2:
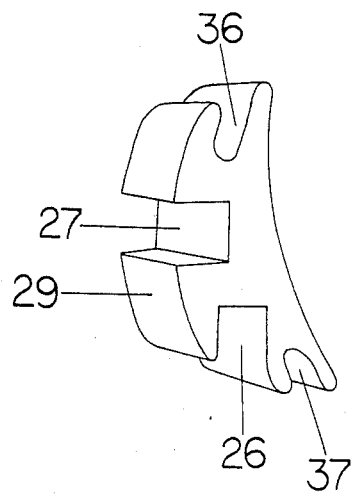
FIG. 2 is an illustration of an oblique view of an orthodontic channel bracket for placement upon the lingual surface of a maxillary incisor tooth.
Figure 3:
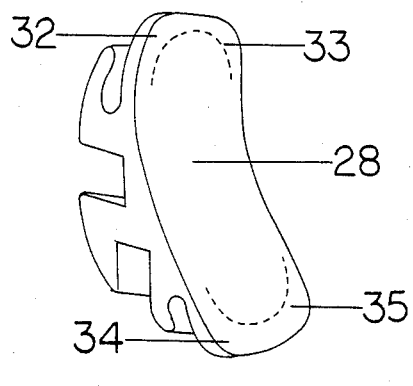
FIG. 3 is an illustration of the side of an orthodontic channel bracket that interfaces with the lingual surface of a maxillary incisor tooth.
Figure 5:
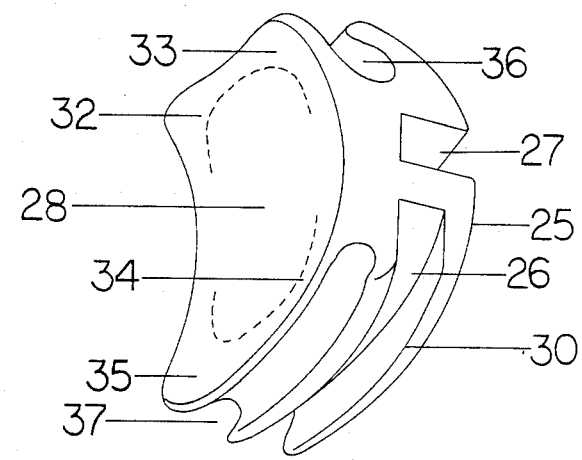
FIG. 5 is an illustration of an oblique view of an orthodontic channel bracket for placement upon the facial surface of a maxillary anterior tooth.
Figure 6:
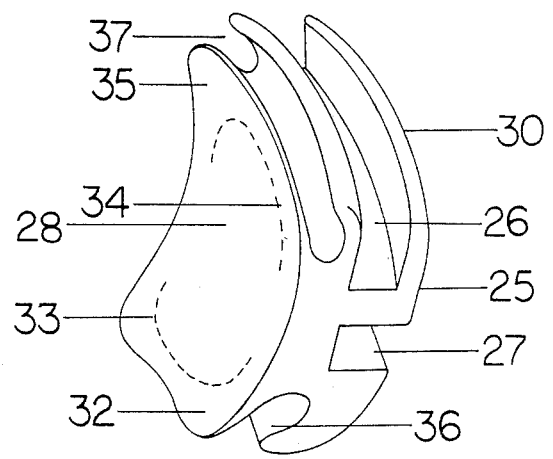
FIG. 6 is an illustration of an oblique view of an orthodontic channel bracket for placement upon the facial surface of a mandibular anterior tooth.

The channel bracket is a mechanical device that has a design and configuration that makes it suitable for attachment upon an area of the clinical crown of a tooth, and to be used in providing orthodontic treatment. FIGS. 1,2,3,4,5,6. The channel bracket has two channels in adjacent areas of the bracket. FIG. 1 (26,27). Each of these two channels can receive an orthodontic arch wire within its walls. The walls of each channel form a rectangular shape. The channel brackets, illustrated in FIGS. 1,2,3, are similar to channel brackets that would be placed upon the lingual surface of maxillary incisor teeth. The channel brackets, illustrated in FIGS. 5,6, are similar to channel brackets that would be placed upon the facial surface of anterior teeth. FIG. 5 illustrates a maxillary bracket and FIG. 6 illustrates a mandibular bracket.

The channel bracket has width, height, and depth. The channel bracket is usually placed upon either the facial or lingual surface of the clinical crown of a tooth. The side of the bracket that interfaces with the surface of a tooth, FIGS. 3,5,6 (28), is called the base of the bracket. When the bracket has the base attached to the facial surface of a tooth, the side of the bracket opposite to the base is called the facial surface of the bracket. FIGS. 5,6 (25). When the bracket has the base attached to the lingual surface of a tooth, the side of the bracket opposite to the base is called the lingual surface of the bracket. FIG. 2 (29).

The side of the bracket that faces toward the gingival area of a tooth is called the gingival side of the bracket. The side of the bracket that faces toward the occlusal side of a tooth is called the occlusal side of the bracket. The side of the bracket that faces toward the anterior midline of the dental arch is called the mesial side of the bracket. The side of the bracket that faces away from the anterior mid-line of the dental arch is called the distal side of the bracket.

The channel bracket of the invention has a channel traversing the occlusal area of the bracket from mesial to distal, and the open side of the channel is facing occlusally. FIG. 1 (26). This channel is called the vertical channel of the bracket. This channel receives its depth with walls that are vertical to the occlusal plane. The channel bracket also has a channel traversing the facial surface of the bracket from mesial to distal and the open side of this channel faces facially, when the base of bracket is upon the facial surface of a tooth. FIG. 5 (27). When the bracket base is upon the lingual surface of a tooth, the channel traverses the lingual surface of the bracket from mesial to distal and the open side of the channel faces lingually. FIG. 2 (27). This channel is called the horizontal channel. This channel receives its depth with walls that are horizontal to the occlusal plane. The vertical channel is rectangular in shape. FIG. 1 (26). The rectangular shape is placed into the channel bracket at an angulation, to the surface of the crown of the tooth upon which it is to be placed, that corresponds to the preferred angulation and position that the specific tooth should have in relation to: the occlusal plane, the supporting oral tissues, and the function of the dental facial complex. Therefore, each tooth in the dental arch has a preferred angulation and position at which the vertical channel of the channel bracket is positioned, in the occlusal area of the channel bracket.

The horizontal channel of the channel bracket has the same interior dimensions and the same interior rectangular angulations as the corresponding traversing sides of the vertical channel of the channel bracket. The vertical channel, opens toward the occlusal side of the bracket and therefore the walls of the vertical channel traverse along a curvature similar to the preferred curvature of aligment and position of the teeth in a dental arch. FIGS. 5,6 (30). The horizontal channel is open on the facial side of a bracket, FIGS. 5,6 (27), that is placed upon the facial surface of a tooth; and is open on the lingual surface of a bracket placed upon the lingual surface of a tooth. FIG. 1 (27). The curvature of the walls of the vertical channel will be convex in curvature when the bracket is upon the facial surface of an anterior tooth, and concave in curvature when the bracket is upon the lingual surface of an anterior tooth.

The vertical channel and the horizontal channel have corresponding walls of the same angulation to each other and the same width of the channel; so that an orthodontic square arch wire of a specific size will fit identically within the walls and their angular relation, in either the vertical or horizontal channel, if the arch wire is along a similar plane in space to the vertical or horizontal channel. If the lingual-facial size of the vertical channel is 0.022 of an inch, FIG. 1 (26), and the occlusal-gingival size of the horizontal channel is 0.022 of an inch, FIG. 1 (27); a square orthodontic arch wire with a diameter of 0.022 of an inch will fit within the confining walls of either the vertical or horizontal channel.

The facial or lingual surface of a bracket is somewhat semicircular in contour. FIG. 1 (31). The position of the vertical channel into the surface of the bracket is determined by the preferred angulation and position of the particular tooth, and the relation of a dental arch shaped wire to the preferred position and angulation of the particular tooth, along the preferred occlusal plane. The vertical channel, FIG. 2 (26), traverses the bracket from mesial to distal in the occlusal area of the channel bracket. The walls of the vertical channel, FIG. 2 (26), will be positioned to produce: torquing, rotational, tipping, facial and lingual directional forces, and intrusive forces; when suitably intercoupled with an orthodontic arch wire. The walls of the horizontal channel, FIG. 1 (27), have the same angular relation as the corresponding walls of the vertical channel and forming a rectangle positioned to produce: torquing, tipping, antirotational, facial and lingual directional forces and intrusive and extrusive forces; when suitably intercoupled with an orthodontic arch wire.

The vertical channel, FIG. 2 (26), is particularly useful in providing rotational forces precisely and efficiently. The vertical channel provides for the placement of an arch wire in an occlusal-gingival direction into the vertical channel. The occlusal-gingival placement of an arch wire is particularly useful when placing segments of an arch wire instead of a continuous dental arch shaped wire; and also when placing orthodontic arch wires on the lingual aspect of teeth. The preciseness and efficiency of vectors of force for the movement of teeth are related to the intercoupling of the channel walls of the bracket with the arch wire or segment thereof. The open side of a channel does not confine the arch wire, and therefore any confinement at the open side of the channel results from the ligation of the arch wire into the channel.

The presence of both a vertical channel and a horizontal channel and the selective or simultaneous use thereof, increases the spectrum of forces that can be precisely and efficiently produced by the confinement of an arch wire within the specific walls of a traversing channel of a channel bracket. Therefore, the open side of the horizontal channel, FIG. 2 (27), is not efficient in producing rotational forces along the occlusal-apical axis of a tooth. The vertical channel, FIG. 2 (26), can be used with an arch wire to produce specific rotational forces along the occlusal-apical axis of a tooth. The incorporation of a vertical channel in a channel bracket, in the manner described in this invention, is new and useful. The tube bracket, and the supplemental tube bracket, described later in this text, provides a means for the simultaneous placement of an arch wire and an orthodontic tube in an occlusal-gingival direction. The vertical channel of the channel bracket facilitates specifically this simultaneous placement.

The side of the channel bracket that interfaces with the surface of the tooth upon which it is placed is called the base of the channel bracket. FIGS. 3,5,6 (28). The base of the bracket is not designed to be fully and continuously in contact with the surface of the tooth upon which it is placed. The base of the bracket is designed to have selected areas of contact with the tooth surface. FIGS. 3,5,6, (32,33,34,35,). The selection of these areas of contact is made by giving consideration to: the stability of the bracket upon the tooth surface, the prevalance of variations in the tooth surface of specific areas of the clinical crowns of teeth, the control of adhesive material, and the potential escape of excess adhesive material from the area between the interfacing surfaces of the bracket and the tooth surface.

The areas of the base of the bracket, not selected for areas of contact with the surface of the tooth, are concave in contour. The degree of concavity of these areas of the base increases from along the margins of the base toward the middle area of the base of the bracket. FIGS. 3,5,6 (28). The concave shape of some areas of the base of the bracket, decrease or nullify the effects upon the fit and stability of the bracket, that may be caused by variations of the tooth surface, in one person as compared to another person. The concave shaped areas of the base decrease the squashing effect of the adhesive material between the bracket base and the tooth, and thereby assists in the control of the adhesive material that may flow out from under the base of a bracket, when a bracket is placed upon a tooth. The areas of the base usually selected for contact upon the tooth surface are: along the gingival area of the base of the bracket, FIG. 3 (32,33), and along the occlusal areas of the base of the bracket, FIG. 3 (34,35). The areas of the base of the bracket not selected to contact the tooth surface, allow the adhesive material to accommodate to variations in the tooth surface.

Figure 7:
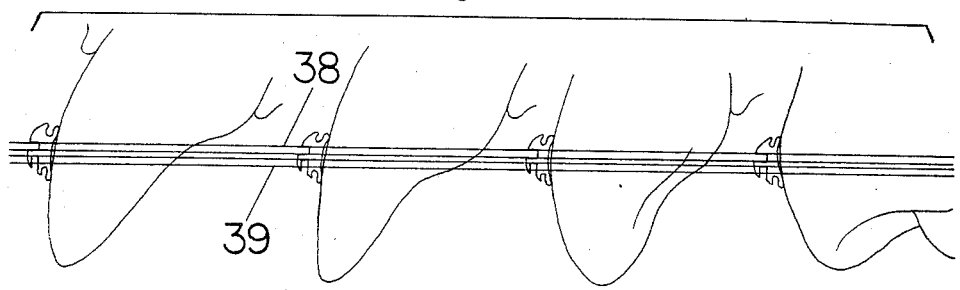
FIG. 7 is an illustration of a lateral view of orthodontic channel brackets upon the facial surface of maxillary, anterior, and bicuspid teeth, and of a supplemental tube bracket intercoupled with an orthodontic tube bracket upon a maxillary molar tooth; and the relationship of these components along a continuous plane, and the relationship of the vertical and horizontal channels of the orthodontic channel brackets and of the tubes of the supplemental tube bracket, to each other and to the continuous plane.
Figure 7:
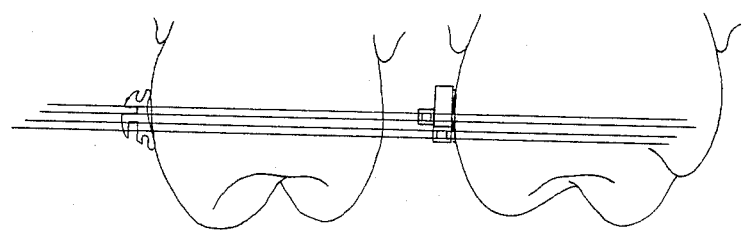
Figure 8:
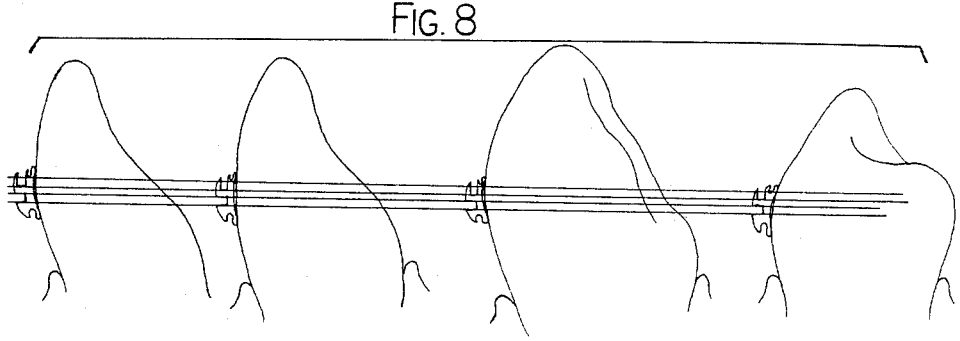
FIG. 8 is an illustration of a lateral view of orthodontic channel brackets upon the facial surface of mandibular, anterior, bicuspid, and second molar teeth, and of a supplemental tube bracket intercoupled with an orthodontic tube bracket upon a first molar tooth; and the relationship of these components along a continuous plane, and the relationship of the vertical and horizontal channels of the orthodontic channel brackets and of the tubes of the supplemental tube bracket, to each other and to the continuous plane.
Figure 8:
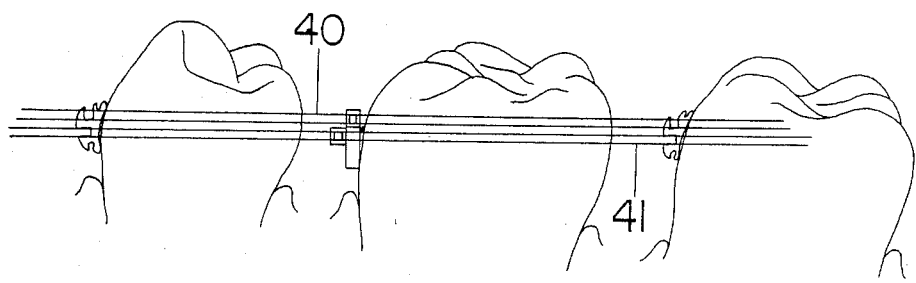
Figure 9:
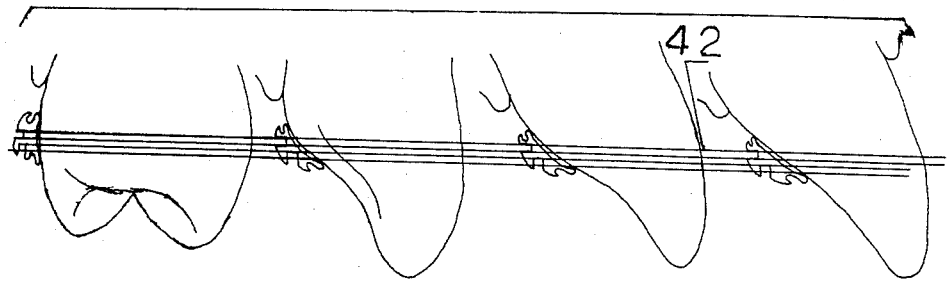
FIG. 9 is an illustration of a lateral view of orthodontic channel brackets upon the lingual surface of maxillary and mandibular, anterior, bicuspid, and second molar teeth, and of a supplemental tube bracket intercoupled with an orthodontic tube bracket upon the first molar teeth; and the relationship of these components along a continuous plane, and the relationship of the vertical and horizontal channels of the orthodontic channel brackets and the tubes of the supplemental tube bracket, to each other and to the continuous plane.
Figure 9:
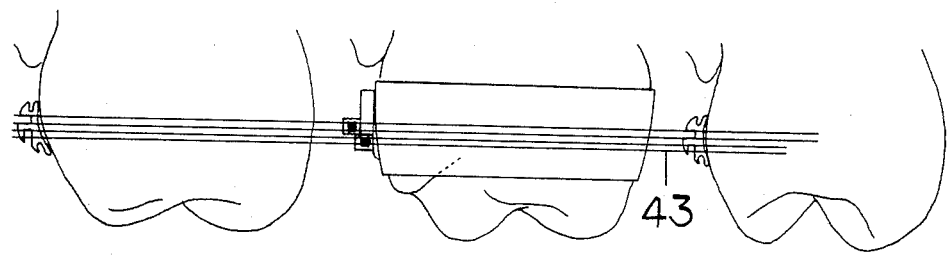
Figure 9:
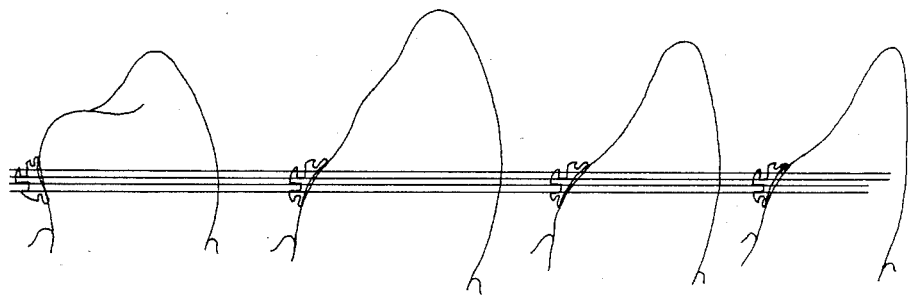
Figure 9:
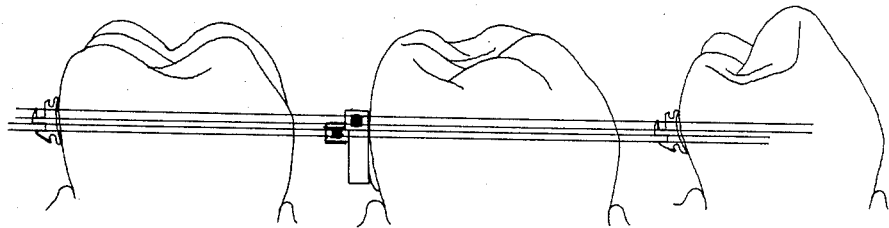

The general configuration of the base of the brackets will vary in relation to the areas of the crowns of the teeth upon which they will be placed. FIGS. 7,8,9. However, the angular relation of the walls of the vertical channel of the channel bracket to the crown of the tooth is determined by the preferred position that each individual tooth should occupy in the dental arch. When the channel brackets are placed upon the lingual surface of maxillary anterior teeth, FIG. 9, some of the base of the bracket may rest upon the eminence of the cingulum of the tooth. This position of the bracket facilitates the use of an arch wire that follows a plane parallel to the occlusal plane. The positioning of the bracket with some of the base upon the eminence of the cingulum of the tooth, also provides for more space between the occlusal margin of the bracket and the incisal edge of the tooth; to accommodate to the overbite that may exist of the mandibular to the maxillary teeth, when the teeth are in occlusion.

There are prevailing angulations at which teeth are placed in the dental arch in certain relationships of the bones of the dental facial complex. Therefore, there are prevailing sets of angulations of teeth, commonly found in specific classes of malocclusion of teeth. This influences the preferred angular position of the channels of the channel bracket to the crown of the tooth in treating specific types of malocclusion.

The channel bracket of the invention has areas shaped to receive orthodontic ligatures at the gingival and occlusal areas of the channel bracket, FIGS. 2,5,6 (36,37). The ligature receiving area at the gingival area of the bracket, FIGS. 2,5,6 (36), is larger than at the occlusal area, to accommodate more than a single ligation, when necessary, in some orthodontic treatment procedures.

The channel brackets are placed upon those areas of the crowns of teeth that facilitate the use of an orthodontic arch wire that follows along a continuous plane. FIGS. 7,8,9. The position of the vertical and horizontal channels being at identical corresponding angles to each other, make it possible to place an arch wire in either channel, and for that arch wire to follow along a continuous plane. FIG. 7 (38,39), FIG. 8 (40,41), FIG. 9 (42,43).

Figure 4:
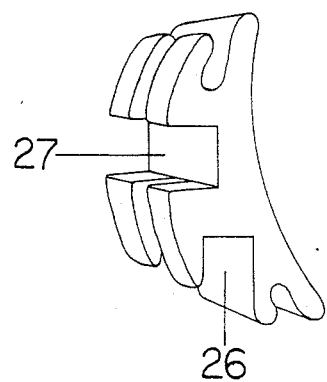
FIG. 4 is an illustration of an orthodontic channel bracket of a siamese type, having two halves of similar design and configuration and joined together by a common base portion of the orthodontic channel bracket.

The siamese type of bracket, FIG. 4, is advantageously used on teeth that have a very convex surface. The convexity of the base of the bracket following the convexity of the tooth, places the ligation receiving areas near the mesial and distal borders of the convexity of the bracket. This position of the ligation areas to receive ligatures, allows for the channel bracket to have less thickness at the middle portion of the bracket and for the channels of the bracket to be located nearer to the tooth surface.

The base of the channel bracket is suitably scored, or has a mesh type of material attached to the base, so that adhesive material can attach itself firmly to this surface, and to the tooth surface upon which the bracket is placed.

The use of adhesive materials to attach orthodontic brackets to the surfaces of teeth, provides a greater flexibility in selecting the area of the tooth upon which the orthodontic bracket may be placed. There are some areas of the clinical crowns where variations in shape are more prevalent in one person as compared to another person. This is particularly evident on the lingual surface of the maxillary anterior teeth on the incisal portion of the cingulum third of the crowns of these teeth.

The orthodontic tube brackets, FIGS. 12,13,15,16,17,18, are usually placed on the facial and/or lingual surface of molar teeth as components of an orthodontic appliance. The tube bracket of the invention has a base that interfaces with the surface of a tooth, FIG. 13 (44). The side of the bracket that is opposite to the base has two tubes upon it, FIG. 13 (45,46). These two tubes are positioned occlusal-gingivally in direction. There is a first-mesial tube and second-distal tube, FIG. 13 (45,46). The interior passageway of each, the first-mesial and second-distal tubes, is rectangular in shape, FIG. 13 (48,47). The rectangular shaped passageway through each of these occlusal-gingival tubes, has a greater size mesial-distally than lingual-facially. As an example; the mesial-distal size of the rectangular shape may be 0.045 of an inch, and the lingual-facial size of the rectangular shape may be 0.022 of an inch. The mesial wall of the first-mesial tube diverges mesially in an occlusal-gingival direction, FIG. 16 (49). The distal wall of the second distal tube diverges distally in an occlusal-gingival direction. FIG. 16 (50). The distal wall of the first-mesial tube is vertical to the occlusal plane, FIG. 18 (51), and this distal wall of the first-mesial tube and the mesial wall of the second-distal tube are parallel to each other. FIG. 18, (51,52).

There is space between the first and second occlusal-gingival tubes, approximately the size of the mesial-distal width of the first occlusal-gingival tube. FIG. 16 (53). The base of the tube bracket, that interfaces with the surface of the tooth, is not designed to be in full and continuous contact with the surface of the tooth upon which it is placed. There are selected areas of contact positioned near the margins of the base of the tube bracket to provide for the stability and appropriate fit of the tube bracket upon the surface of the tooth. The remaining area of the base of the tube bracket follows in a general way the shape of the tooth, but is concave in contour, to minimize or nullify the effect of variations of the tooth surface, upon the fit and stability of the tube bracket, when it is placed upon the tooth surface. The base of the tube bracket is designed to be in contact with the tooth surface, at and near to the gingival margin of the base of the tube bracket, and at and near the mesial and distal margins of the base of the tube bracket. The mid-occlusal margin of the base of the tube bracket is designed to approximate but not to be in contact with the surface of the tooth. This provides for an escape area for any excess of adhesive material in an occlusal direction and for its easy removal. This lack of contact of the mid-occlusal margin of the base also minimizes or nullifies the effects of variations in contour of the tooth surface upon the fit and stability of the tube bracket. The middle areas of the base of the tube bracket are designed to be concave in contour to minimize or nullify the effects of variations in the contour of the tooth surface, upon the fit and stability of the tube bracket, in one person as compared to another person.

Figure 10:
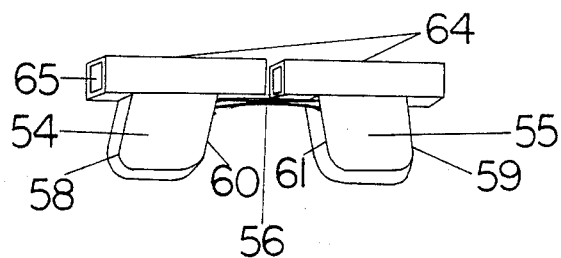
FIG. 10 is an illustration of the supplemental tube bracket of the invention.
Figure 11:
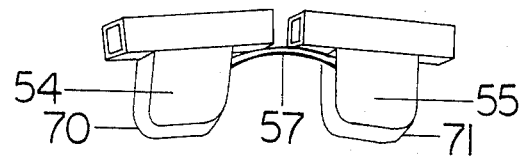
FIG. 11 is an exaggerated illustration of the relationship of the components of the supplemental tube bracket, when the bar is flexed that connects the first-mesial and second-distal posts of the supplemental tube bracket and thereby facilitates the insertion of the base components of the supplemental tube bracket into the orthodontic tube bracket.
Figure 12:
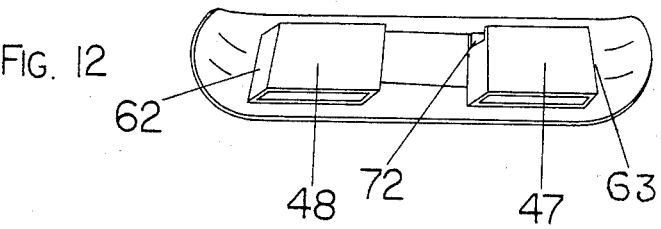
FIG. 12 is an illustration of the orthodontic tube bracket of the invention.
Figure 14:
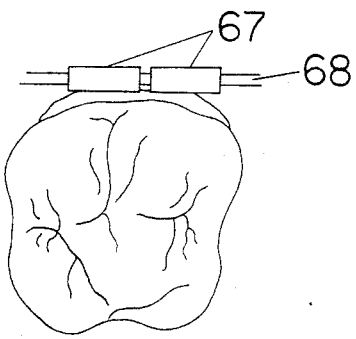
FIG. 14 is an illustration of the occlusal view of a supplemental tube bracket after the base of the supplemental tube bracket has been placed into the orthodontic tube bracket, and with an orthodontic arch wire in the passageway of the horizontal tube of the supplemental tube bracket.

The supplemental tube bracket, FIGS. 10,11,14, is composed of a base of the bracket that is comprised of a first-mesial and second-distal post that are occlusal-gingival in direction. FIG. 10 (54,55). These two posts are divided by a space approximately one and one fourth times the mesial-distal width of the first mesial post. There is a metal bar that connects the first-mesial and second-distal posts, FIG. 10 (56). This connection with the bar is near the occlusal area of the first-mesial and second-distal posts of the supplemental tube bracket. This connecting bar is small in diameter and is made of metal with adequate properties of elasticity and resilience. The size at the middle of this connecting bar may be 0.014 of an inch occlusal gingivally, and 0.022 of an inch lingual facially. This bar is slightly concave mesial distally to cause the bar to flex more easily at the middle of the bar. When the supplemental tube bracket flexes at the mid-section that connects the first-mesial and seond-distal posts of the supplemental tube bracket, FIG. 11 (57), the first-mesial and the second-distal posts of the supplemental tube bracket, FIG. 11 (54,55), are allowed to enter the first-mesial and second-distal occlusal-gingival tubes of the tube bracket. FIG. 12 (48,47).

The base of the supplemental tube bracket, FIG. 10 (54,55,56), fits into the two occlusal-gingival tubes of the tube bracket. FIG. 12 (48,47). The base of the supplemental tube bracket has a first-mesial post-shaped area, FIG. 10 (54), receivable into the first-mesial occlusal-gingival tube of the tube bracket, FIG. 12 (48), and a second-distal post-shaped area, FIG. 10 (55), receivable into the second-distal occlusal-gingival tube of the tube bracket, FIG. 12 (47). The first-mesial post and the second-distal post of the supplemental tube bracket have identical angular divergencies on both the mesial and distal sides of the first-mesial and second-distal posts of the supplemental tube brackets. FIG. 10 (58,59,60,61). This divergence is like that present in the mesial wall of the first-mesial and the distal wall of the second-distal occlusal-gingival tubes of the tube bracket, FIG. 12 (62,63). The mesial and distal sides of the first-mesial post, and the mesial and distal sides of the second-distal post of the supplement tube bracket, have the same and equal angular divergence of each of these sides of the first-mesial post as compared to each side of the second-distal post, FIG. 10 (58,59,60,61).

The supplemental tube bracket has a tube attached to the occlusal aspect of the first-mesial and second-distal posts of the supplemental tube bracket. FIG. 10 (64). This tube is referred to as a horizontal tube of the supplemental tube bracket. This horizontal tube is divided at its middle vertically and thereby forms two halves. The mesial half is attached to the first-mesial post, FIG. 10 (54), and the second half is attached to the second-distal post of the supplemental tube bracket, FIG. 10 (55).

The passageway, FIG. 10 (65), is identical in size and angulation, and is along an identical plane in space, in both halves of this divided tube. The separation of this tube into two halves allows for the flexation of the bar that connects the first-mesial and second-distal posts of the supplemental tube bracket. FIG. 11 (57). There also can be two tubes that are horizontal to the occlusal plane that are part of the supplemental tube bracket. FIG. 21 (66). Both of these horizontal tubes are divided to allow for the flexation of the center component of the supplemental tube bracket. However, each of the horizontal divided tubes act as a single tube when receiving an orthodontic arch wire. FIG. 14 (67,68). The passageway through the horizontal tube or tubes is rectangular in shape. The size of this rectangular passageway, FIG. 19 (69), through the horizonal tube has a specific relationship to the amount of flexation that can occur of the bar that connects the first-mesial and second-distal posts of the supplemental tube bracket, FIG. 11 (57), when an arch wire of a specific size is present in the horizontal tube, FIG. 14 (68), prior to the intercoupling of the supplemental tube bracket, and the tube bracket. If the supplemental tube bracket, FIG. 10, is intercoupled with the tube bracket, FIG. 12, before the arch wire is placed through the horizontal tube, FIG. 14 (67), then an arch wire that fills the passageway of the horizontal tube can be placed therein. When the arch wire in the passageway of a horizontal tube of the supplemental tube bracket is of sufficient size to prevent the flexing of the bar that connects the first-mesial and second-distal posts of the supplemental tube bracket; the resulting effect is a locking of the base of the supplemental tube bracket, in the occlusal-gingival tubes of the tube bracket. If the supplemental tube bracket, FIG. 10, is intercoupled with the tube bracket, FIG. 12, after the arch wire has been placed through the passageway of the horizontal tube, FIG. 10 (65), the size of the arch wire must be sufficiently smaller occlusal-gingivally than is the passageway through the horizontal tube, to allow for the flexing of the bar of the supplemental tube bracket, FIG. 11 (57), sufficiently, to make possible the intercoupling of the posts of the supplemental tube bracket, FIG. 11 (54,55), into the occlusal-gingival tubes of the tube bracket. FIG. 12 (48,47).

The first mesial and second distal posts of the supplemental tube bracket are rounded sufficiently at the gingival areas of these posts, FIG. 11 (70,71), so that the divergence of the first-mesial post to the second-distal post will not prevent them from being inserted into the occlusal-gingival tubes of the tube bracket, as the bar flexes that connects the first-mesial post to the second-distal post of the supplemental tube bracket. The angular divergence of the posts of the supplemental tube bracket, FIG. 10 (58,59), and the angular divergence of the occlusal-gingival tubes of the tube bracket, FIG. 12 (62,63), and the contour of the gingival area of the posts of the supplemental tube bracket; FIG. 11 (70,71) are all mathematically coordinated to allow the posts of the supplemental tube bracket to be received into the occlusal-gingival tubes of the tube bracket. Therefore, the following, mathematical values are listed to describe more fully the relationship of the sizes and shapes of these components of the invention.

The size of the passageway through the horizontal tube of the supplemental tube bracket. FIG. 10 (65).

Figure 13:
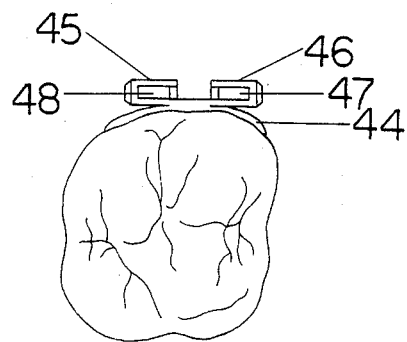
FIG. 13 is an illustration of an occlusal view of the orthodontic tube bracket attached upon the surface of a molar tooth.

| | |
|---|---|
| Occlusal-gingivally | .028 of an inch |
| Lingual-facially | .022 of an inch |
| Divergence of the first-mesial post of the supplemental tube bracket FIG. 10 (58) | .006 of an inch |
| Divergence of the second-distal post of the supplemental tube bracket FIG. 10 (59) | .006 of an inch |
| Divergence of the mesial side of the first mesial occlusal-gingival tube of the tube bracket FIG. 12 (62) | .006 of an inch |
| Divergence of the distal side of the second-distal occlusal-gingival tube of the tube bracket FIG. 12 (63) | .006 of an inch |
| The size of the passageway of the first-mesial and second-distal occlusal-gingival tubes of the tube bracket FIG. 13 (48,47) | .045 of an inch mesial-distally and .022 of an inch lingual-facially |

The horizontal tube of the supplemental tube bracket is divided at the middle area of its length, and therefore allows for the flexing of the bar of the supplemental tube bracket that connects the first-mesial and second-distal posts of the supplemental tube bracket. FIG. 11 (57). The flexing of this bar must be sufficient to nullify the divergence of 0.006 of an inch, of each, the first-mesial and the second-distal posts, of the supplemental tube bracket. This flexing of the bar reduces the divergence of the first-mesial and second-distal posts to zero, FIG. 11, and therefore, the posts can enter the passageway of the first-mesial and second-distal occlusal-gingival tubes of the tube bracket. FIG. 12 (48,47).

The maximum size of a wire that can occupy the passageway of the horizontal tube of the supplemental tube bracket, before the posts of the supplemental tube bracket are placed into the occlusal-gingival tubes of the tube bracket, is a square arch wire 0.022 of an inch by 0.022 of an inch in diameter. The passageway through the horizontal tube of the supplemental tube bracket is 0.028 of an inch occlusal-gingivally and 0.022 of an inch lingual-focially. This will allow each end of the horizontal tube to move 0.006 of an inch occlusal-gingivally before being restrained by a wire 0.022 of an inch in diameter in the passageway of the horizontal tube of the supplemental tube bracket. The position of the horizontal tube or tubes is along a plane parallel to the preferred occlusal plane of the teeth, and along a plane to intercouple with the vertical or horizontal channels of the channel brackets, that have been placed on teeth in the dental arch that are involved in the use of the appliance in orthodontic treatment procedures.

There is a notched area, FIG. 12 (72), in the occlusal aspect of the distal wall of the first-mesial occlusal-gingival tube and mesial wall of the second-distal occlusal-gingival tube of the tube bracket. This notched area accommodates the position of the connecting flexible bar, FIG. 11 (57), component between the first-mesial and second-distal posts of the supplemental tube bracket when the supplemental tube bracket is inter-coupled with the tube bracket. FIG. 12.

When the orthodontic tube bracket is placed upon the facial side of a tooth it is sometimes necessary for treatment purposes to have a tube on it, that is in a general way horizontal to the occlusal plane, FIGS. 15,17, (73), as a component of the tube bracket. The horizontal tube, FIG. 15 (73), is used to receive into the passageway of the tube, components of an orthodontic mechanism that may be used in orthodontic treatment. The horizontal tube is divided into two halves. The mesial half is attached to the first-mesial occlusal-gingival tube of the tube bracket and the distal half is attached to the second-distal occlusal-gingival tube of the tube bracket. The divided horizontal facial tube is attached near the gingival area of the facial side of the occlusal-gingival first-mesial and second-distal tubes of the tube bracket.

The arch wires of the invention, FIG. 22, are designed to advantageously use the tube bracket, FIG. 23, of the invention. An arch wire of the invention, FIG. 22, is shaped to intercouple with the divergent occlusal-gingival tubes of the tube bracket, FIG. 23 (48,47), and to progress in a mesial and/or distal direction from the intercoupling area of the arch wire. The diameter of the arch wire may vary as necessary for treatment procedures. The arch wire may be continuous along the entire dental arch, or may be along a segment of the dental arch. The arch wire or segment thereof may be, round, square, or rectangular, as it progresses from the area of the arch wire that intercouples with the occlusal-gingival tubes of the tube bracket. The arch wire is shaped, FIG. 22, to fit into the first-mesial and second-distal occlusal-gingival tubes of tube bracket. FIG. 23 (48,47).

The divergence of the first-mesial and second-distal posts of the arch wire, FIG. 22 (74,75), designed to intercouple with the tube bracket, FIG. 23, are in identical divergence to the divergence of the first-mesial and the second-distal posts of the supplemental tube bracket, FIG. 10 (54,55), described previously in this text. The flexing of the interval of the arch wire between the first-mesial and second-distal posts of the arch wire, FIG. 22 (76), allows for the intercoupling of the arch wire with the occlusal-gingival first-mesial and second-distal tubes of the tube bracket. FIG. 23 (48,47). This provides for the retention of the arch wire within the tube bracket. The new and useful aspects of the arch wire are found in the advantageous intercoupling of the arch wire with the first-mesial and second-distal occlusal-gingival tubes of the tube bracket, and the insertion of the arch wire in an occlusal-gingival direction, and thereby can be intercoupled simultaneously with the vertical channel of the channel brackets present upon teeth along the dental arch. FIGS. 7,8,9.

Conventional type orthodontic arch wires may be used with the horizontal tube or tubes of the supplemental tube bracket. The supplemental tube bracket provides for the insertion of an arch wire and the supplemental tube bracket simultaneously, if the arch wire is of a size to allow for the flexing of the middle bar of the supplemental tube bracket, sufficiently to allow for the insertion of the first-mesial and second-distal posts of the supplemental tube bracket into the orthodontic tube bracket. If an arch wire is placed into the passageway of the divided horizontal tube, FIG. 10 (65), after the base of the supplemental tube bracket has been placed into the occlusal-gingival tubes of the tube bracket, FIG. 12 (48,47), the arch wire may fully occupy the passageway of the horizontal tube of the supplemental tube bracket. This will result in locking the base of the supplemental tube into the tube bracket, because the bar cannot flex between the first-mesial and second-distal posts of the supplemental tube bracket. The ability to insert simultaneously both the supplemental tube bracket and an arch wire therein, FIG. 14 (67,68), in an occlusal-gingival direction, is particularly useful in treatment procedures performed on the lingual aspect of teeth.

The insertion of an orthodontic arch wire in an occlusal-gingival direction is particularly useful when the vertical channel, FIGS. 1,2,4,5,6 (26), of the channel brackets of the invention are used in treatment procedures.

The arch wires of the invention may be intercoupled with the tube bracket on either the facial, FIG. 24 (77), or the lingual, FIG. 24 (78), aspects of a tooth. Extending from the intercoupling area, the arch wire may be of various sizes and shapes. The shape and use of the intercoupling area of the arch wire, FIG. 22 (74,75,76), is a new and useful portion of the arch wire of this invention.

In providing orthodontic treatment the components of an orthodontic appliance provide a means to exert forces upon the teeth and the structures of the dental facial complex. The orthodontic appliance is usually used to move teeth within the bone that supports them. There are times when parts of the appliance or the entire appliance may be used as an anchor unit or units to facilitate the imposition of forces on the musculature and other components of the oral-facial complex. The appliance of the invention provides a means to apply a broad spectrum of forces that can be used to move a tooth or teeth. The appliance also provides, because of the configuration and design of the components of the appliance; a means for stabilizing teeth when they are to be used as anchorage units for orthodontic treatment procedures.

The use of adhesive materials to attach orthodontic brackets to the surfaces of teeth allows for a greater flexibility in choosing the areas of the clinical crowns upon which the orthodontic brackets may be placed.

The use of metal components is described in the text and drawings pertaining to this invention. Various other materials, such as plastic materials, and ceramic materials and combinations of materials, may be used to fabricate the components of this invention. It is not the intent of this text, description, and drawings, to limit the types of materials that may be used to provide the components of this orthodontic appliance. It is recognized that new materials may be developed to be used in making the components of the invention.

The descriptive text and drawings of the invention presume that adhesive materials will be used to attach the orthodontic channel brackets and orthodontic tube brackets to the teeth. This is not intended to preclude the attachment of the components of the appliance when practical and suitable, to orthodontic bands that encircle individual teeth, as a means of attaching those components to the teeth, for use in orthodontic treatment procedures.

It should be understood, that the foregoing disclosure and specifications relates to particular and preferred embodiments of the invention, and that it is intended to cover all changes and modifications of the examples of the invention herein chosen for the purposes of the disclosure, which do not constitute departures from the spirit and scope of the invention.

What is claimed is:

1. An orthodontic system for aligning a tooth with respect to an occlusal plane which is adjacent to said tooth, said system comprising a channel bracket and at least one orthodontic arch wire;

said channel bracket having a base means which mounts the channel bracket on a specific area of the surface of said tooth;

said channel bracket having an occlusal side, a gingival side, a mesial side, a distal side, and an outer side which faces in a lingual-facial direction;

channel means including at least one channel formed in the channel bracket and extending from the mesial side to the distal side thereof, said channel means having walls which provide a cross section which is a rectangle in planes which are perpendicular to a mesio-distal direction, said rectangle having one open side which permits the insertion of the arch wire into the channel;

said channel means having at least one curved wall which is vertical with respect to the occlusal plane adjacent to said tooth and is curved when viewed in an occlusal-gingival direction; said channel means also having at least one curved wall which is horizontal with respect to the occlusal plane adjacent to said tooth and is curved when viewed in a lingual-facial direction;

said arch wire lying in said channel and having a rectangular shape which engages said curved walls to exert a tooth-moving force on the bracket;

said bracket having ligature receiving means in its occlusal and gingival sides.

2. An orthodontic system according to claim 1 having a plurality of said brackets which have their said channels receiving said arch wire.

3. An orthodontic system according to claim 2 wherein there are two said arch wires, said channel means comprising first and second channels formed in the bracket, each of said channels receiving a respective one of said arch wires.

4. An orthodontic system according to claim 3 having a plurality of said brackets which each have said first and second channel receiving said arch wires.

5. An orthodontic system according to claim 3 wherein the open side of first channel faces in an occlusal-gingival direction and the open side of said second channel faces in a lingual-facial direction.

6. An orthodontic system according to claim 5 having a plurality of said brackets which have said first and second channels receiving said arch wires.

7. An orthodontic tube bracket for use in a system for aligning a tooth with respect to an occlusal plane which is adjacent to said tooth,
  said tube bracket having a base means which mounts the tube bracket on a specific area of the surface of said tooth;
  said tube bracket having an occlusal side, a gingival side, a mesial side, a distal side, and an outer side which faces in a lingual-facial direction;
  said tube bracket having two tubes which are separated from each other by a space, each of said tubes having a passageway extending therethrough in an occlusal-gingival direction, each said passageway having a rectangular shape which has a greater size mesial-distally than lingual-facially, each of said tubes having a gingival end and an occlusal end, each said tube having a first wall with an external surface which faces said between the tubes, said first walls lying vertical with respect to the occlusal plane, each of said tubes having a second wall which is most distant from the space between the tubes, said second walls diverging from each other from the occlusal end of the tube to the gingival end of the tube.

8. An orthodontic tube bracket according to claim 7 in combination with a supplemental tube bracket, said supplemental tube bracket having at least one supplemental tube which has a passageway which extends in a mesial-distal direction, said supplemental tube being mounted on a pair of posts which are inserted in said passageways of said tubes of the orthodontic tube bracket, said posts of the supplemental tube bracket being resiliently connected together and having surfaces which diverge from each other in an occlusal-gingival direction to conform to the divergence of the second walls of the orthodontic tube bracket.

9. The invention according to claim 8 wherein the supplemental tube bracket has two said supplemental tubes, each of said supplemental tubes being mounted on one of said posts, a resilient bar connecting said posts to each other, said tubes of said orthodontic tube bracket having nothces in the occlusal ends of said first walls, said resilient bar extending through said notches.

10. The invention according to claim 8 having an orthodontic arch wire inserted in a said supplemental tube.

11. The invention according to claim 8 wherein the supplemental tube bracket has two said supplemental tubes, said supplemental tubes being aligned with each other in a mesial-distal direction.

12. The invention according to claim 8 wherein the supplemental tube bracket has two said supplemental tubes, said supplemental tubes being out of alignment with each other in a mesial-distal direction.

13. The invention according to claim 12 having two orthodontic arch wires which are inserted in different ones of said supplemental tubes.

14. An orthodontic tube bracket according to claim 7 in combination with an orthodontic arch wire which is locally bent to provide two posts which are inserted in said passageways of said tubes of the orthodontic tube bracket, said posts of the archwire having surfaces which diverge from each other in an occlusal-gingival direction to conform to the divergence of the second walls of the orthodontic tube bracket.

15. A main tube bracket and a supplemental tube bracket in a system for aligning a tooth with respect to an occlusal plane which is adjacent to said tooth,
  said main tube bracket having a base means which mounts the tube bracket on a specific area of the surface of said tooth;
  said main tube bracket havig an occlusal side, a gingival side, a mesial side, a distal side, and an outer side which faces in a lingual-facial direction;
  said main tube bracket having two tubes which are separated from each other by a space, each of said tubes having a passageway extending therethrough in an occlusal-gingival direction, said passageways being angularly divergent with respect to each other;
  said supplemental tube bracket having first and second supplemental tubes each of which has a passageway which is oriented in a mesial-distal direction, a pair of posts, each of said supplemental tubes being mounted on one of said posts, each of said posts being inserted in one of said passageways of said tubes of the main tube bracket, said posts being angularly divergent with respect to each other when the supplemental tubes are aligned with each other in mesial-distal direciton so as to correspond with the angular divergence between said passageways of the main tube bracket.

16. The invention according to claim 15 having an orthodontic arch wire inserted in said supplemental tubes.

17. The invention according to claim 15 wherein the supplemental tube bracket has a third supplemental tube, said third supplemental tube being out of alignment with the first and second supplemental tubes in a mesial-distal direction.

18. The invention according according to claim 17 having two orthodontic arch wires one of which is inserted in the first and second said supplemental tubes, and another of which is inserted in the third supplemental tube.

* * * * *